United States Patent [19]

Lau

[11] Patent Number: 5,087,575

[45] Date of Patent: Feb. 11, 1992

[54] COMPOSITION FOR DETERMINING TRACE AMOUNT OF PROTEIN

[75] Inventor: Arthur L. Y. Lau, Granger, Ind.

[73] Assignee: Miles Inc., Elkhart, Ind.

[21] Appl. No.: 520,072

[22] Filed: May 7, 1990

Related U.S. Application Data

[62] Division of Ser. No. 202,552, Jun. 6, 1988, Pat. No. 4,960,710.

[51] Int. Cl.$^5$ ............................................. G01N 33/48
[52] U.S. Cl. ..................................... 436/166; 436/169; 252/301.5
[58] Field of Search ................ 422/56; 436/63, 66–67, 436/86, 166, 169; 252/301.5

[56] References Cited

U.S. PATENT DOCUMENTS 4,143,080   3/1979   Harders et al. ......................... 436/66

OTHER PUBLICATIONS

Fujita et al., Bunseki Kagaku, vol. 32(12), pp. 379–386, abstract only.

Primary Examiner—Robert J. Warden
Assistant Examiner—Lyle A. Alexander
Attorney, Agent, or Firm—Roger N. Coe

[57] ABSTRACT

A new and improved method and composition for determining the presence and concentration of low to trace amounts of proteins, such as albumin, in a test sample, such as urine. The method includes using a reagent composition capable of interacting with low trace amounts of proteins to produce a visually or instrumentally detectable and/or measurable response. The method can be used in wet assays or in dry test strip assays, wherein the reagent composition is incorporating into a carrier matrix. The new and improved reagent composition, comprising a dye, such as a polyhydroxybenzenesulfonephthalein-type indicator, like pyrocatechol violet; a tungstate, such as ammonium tungstate; and, if necessary, a suitable buffer, is incorporated into the carrier matrix to provide sufficient sensitivity to low to trace protein levels and sufficient color resolution between low to trace protein levels, thereby affording an accurate and trustworthy protein assay of test samples having a low protein concentration.

10 Claims, No Drawings

COMPOSITION FOR DETERMINING TRACE AMOUNT OF PROTEIN

This is a division of application Ser. No. 202,552, filed on June 6, 1988, now U.S. Pat. No. 4,960,710.

FIELD OF THE INVENTION

The present invention relates to a composition and a method of assaying a test sample for the presence and concentration of low to trace amounts of proteins. More particularly, the present invention relates to a new and improved method and composition for assaying a liquid, such as urine, for low to trace amounts of proteins by utilizing a reagent composition including a tungstate-dye complex as the reaction indicator. The reagent composition is incorporated into a carrier matrix, such that a detectable and/or measurable response occurs upon contact of the reagent composition with a test sample containing a low to trace amount of protein. The reagent composition provides sufficient sensitivity to proteins and sufficient color resolution between different protein concentrations in order to accurately detect and/or measure, either visually or by instrument, the protein content of a liquid test sample. In addition, the present invention relates to using a reagent composition including a tungstate-dye complex as the indicator in a method to determine the presence and/or concentration of low to trace amounts of proteins in a test sample by a dry phase, test strip assay procedure or by a wet phase solution assay procedure.

BACKGROUND OF THE INVENTION AND PRIOR ART

Albumin is the most abundant plasma protein, generally constituting slightly over one-half of the total protein in mammalian plasma. In the human body, albumin has the important role of regulating the water balance between blood and tissues, and of functioning as a transport molecule for various compounds, such as bilirubin, fatty acids, cortisol, thyroxine and drugs such as sulfonamides and barbiturates, that are only slightly soluble in water. An albumin deficiency can restrict the transport of slightly water soluble materials throughout the body and a deficiency is signaled in an individual by an abnormal accumulation of serous fluid, or edema. Therefore, it is clinically important to determine whether an individual has a deficiency of serum albumin.

Likewise, it is clinically important to determine if an individual is excreting an excess amount of protein. A normal functioning kidney forms urine in an essentially two step process. Blood flows through the glomerulus, or glomerular region of the kidney. The capillary walls of the glomerulus are highly permeable to water and low molecular weight components of the blood plasma. Albumin and other high molecular weight proteins cannot pass through these capillary walls and are essentially filtered out of the urine so that the protein is available for use by the body. The liquid containing the low molecular weight components passes into the tubules, or tubular region, of the kidney where reabsorption of some urine components, such as low molecular weight proteins; secretion of other urine components; and concentration of the urine occurs. As a result, through the combined processes of the glomerulus and tubules, the concentration of proteins in urine should be minimal to non-existent Therefore, abnormally high amounts of albumin and/or low-molecular weight proteins in urine must be detected and related to a physiological dysfunction.

The relatively high concentration of albumin in the urine of an individual usually is indicative of a diseased condition. For example, the average normal concentration of protein in urine varies from about 2 mg/dL to about 8 mg/dL, with approximately one-third of the total urinary protein being serum albumin. However, in a majority of diseased states, urinary protein levels increase appreciably, such that albumin accounts for from about 60 percent to about 90 percent of the excreted protein. The presence of an abnormal increased amount of protein in the urine, known as proteinuria, is one of the most significant indicators of renal disease, and may be indicative of various other non-renal related diseases.

Therefore, in order to determine if an individual has an albumin deficiency and/or to determine if an individual excretes an excess amount of protein, and in order to monitor the course of medical treatment to determine the effectiveness of the treatment, simple, accurate and inexpensive protein detection assays have been developed. Furthermore, of the several different assay methods developed for the detection and/or measurement of protein in urine and serum, the methods based on dye binding techniques have proven especially useful because dye binding methods are readily automated and provide reproducible and accurate results.

In general, dye binding techniques utilize pH indicator dyes that are capable of interacting with a protein, such as albumin, and that are capable of changing color upon interaction with a protein absent any change in pH. When a pH indicator dye interacts with, or binds to, a protein, the apparent $pK_a$ (acid dissociation constant) of the indicator dye is altered and the dye undergoes a color transition, producing the so-called "protein-error" phenomenon. In methods utilizing the dye binding technique, an appropriate buffer maintains the pH indicator dye at a constant pH to prevent a color transition of the pH indicator dye due to a substantial shift in pH. Due to the "protein-error" phenomena, upon interaction with the protein, the pH indicator dye undergoes a color transition that is identical to the color change arising because of a change in the pH. Examples of pH indicator dyes used in the dry phase assay of proteins that are capable of interacting with or binding to proteins and exhibiting "protein-error" color transitions include tetrabromophenol blue and tetrachlorophenol-3,4,5,6-tetrabromosulfophthalein.

Although pH indicator dyes have been used extensively in protein assays, several problems and disadvantages still exist in protein assay methods utilizing indicator dyes. For example, methods based upon pH indicator dyes either cannot detect or cannot quantitatively differentiate between protein concentrations below approximately 15 mg/dL. In addition, although several simple semiquantitative tests and several complex quantitative tests are available for the determination of the total protein content in a test sample, the majority of these assay methods, with the notable exception of the simple colorimetric reagent test strip, require the precipitation of protein to make quantitative protein determinations.

The colorimetric reagent test strip utilizes the previously discussed ability of proteins to interact with certain acid-base indicators and to alter the color of the indicator without any change in the pH. For example, when the indicator tetrabromophenol blue is buffered to maintain a constant pH of approximately 3, the indicator imparts a yellow color to solutions that do not contain protein. However, for solutions containing protein, the presence of protein causes the buffered dye to impart either a green color or a blue color to the solution, depending upon the concentration of protein in the solution.

Some colorimetric test strips used in protein assays have a single test area consisting of a small square pad of a carrier matrix impregnated with a buffered pH indicator dye, such as tetrabromophenol blue. Other colorimetric test strips are multideterminant reagent strips that include one test area for protein assay as described above, and further include several additional test areas on the same strip to permit the simultaneous assay of other urinary constituents. For both types of colorimetric test strips, the assay for protein in urine is performed simply by dipping the colorimetric test strip into a well mixed, uncentrifuged urine sample, then comparing the resulting color of the test area of the test strip to a standardized color chart provided on the colorimetric test strip bottle.

For test strips utilizing tetrabromophenol blue, buffered at pH 3, as the indicator dye, semiquantitative assays for protein can be performed and are reported as negative, trace, or one "plus" to four "plus". A negative reading, or yellow color, indicates that the urine contains no protein, as demonstrated by the lack of a color transition of the indicator dye. A trace reading may indicate from about 5 to about 20 mg/dL of protein in the urine. The one "plus" to four "plus" readings, signified by color transitions of green through increasingly dark shades of blue, are approximately equivalent to urine protein concentrations of 30, 100, 300, and over 2000 mg/dL, respectively, and serve as reliable indicators of increasingly severe proteinuria.

In accordance with the above-described method, an individual can readily determine, visually, that the protein content of a urine sample is in the range of 0 mg/dL to about 30 mg/dL However, the color differentiation afforded by the presently available commercial test strips is insufficient to allow an accurate determination of protein content in urine between 0 mg/dL and about 15 mg/dL. The inability to detect and differentiate between low protein concentrations is important clinically because a healthy patient usually has a urine protein level in the range of about 10 mg/dL to about 20 mg/dL. Therefore, it could be clinically important to know more precisely the urine protein content of an individual, rather than merely estimating the protein content at some value less than about 30 mg/dL.

Of course, the protein content of a urine sample can be determined more precisely by semiquantitative protein precipitation techniques or by quantitative 24 hour protein precipitation techniques. However, these tests are time consuming and relatively expensive. Furthermore, the precipitation tests must be run in a laboratory by trained personnel, and therefore are unavailable for the patient to perform at home to quickly determine urine protein content and to monitor the success or failure of a particular medical treatment Therefore, it would be extremely advantageous to have a simple, accurate and trustworthy method of assaying urine for a low to trace protein content that allows visual differentiation of protein levels in the ranges of 0 mg/dL to about 5 mg/dL, about 5 mg/dL to about 10 mg/dL, about 10 mg/dL to about 20 mg/dL, and about 20 mg/dL to about 30 mg/dL, and upwards to between about 100 mg/dL to about 300 mg/dL. By providing such an accurate method of determining a low to trace urine protein concentration in an easy to use form, such as a dip-and-read test strip, the urine assay for low to trace amounts of protein can be performed by laboratory personnel to afford immediate test results such that a diagnosis can be made without having to wait up to one day for assay results, and medical treatment can be commenced immediately. In addition, the test strip method can be performed by the patient at home to more precisely monitor low to trace levels of protein in urine and/or the success of the medical treatment the patient is undergoing.

As will be described more fully hereinafter, the method of the present invention allows the fast, accurate and trustworthy assay for low to trace levels of protein in urine by utilizing a test strip that includes a reagent composition incorporating a tungstate-dye complex. The tungstate-dye complex reagent composition improves the sensitivity of the assay and provides sufficient visual color resolution between different protein concentrations, and therefore allows urine protein concentrations at levels of approximately 30 mg/dL or less to be accurately determined. In addition, the method of the present invention also can be used to determine the presence and/or concentration of higher concentrations of proteins, such as from about 100 mg/dL to about 2000 mg/dL, in a test sample.

The level of proteinuria exhibited by an individual depends upon the precise nature of the clinical and pathological disorder and upon the severity of the specific disease. Proteinuria can be intermittent or continuous, with transient, intermittent proteinuria usually being caused by physiologic or functional conditions rather than by renal disorders. Therefore, accurate and thorough assays of urine and other liquid test samples for protein must be available for both laboratory and home use. The assays must permit the detection and measurement even of low to trace concentrations of proteins, such that a correct diagnosis can be made and correct medical treatment implemented, monitored and maintained. In addition, it would be advantageous if the protein assay method for low to trace concentrations of protein could be utilized in a dip-and-read format for the easy and economical, qualitative and/or semiquantitative determination of protein in urine or other liquid test samples.

Furthermore, any method of assaying for protein in urine or other test samples must yield accurate, trustworthy and reproducible results by utilizing a reagent composition that undergoes a color transition as a result of an interaction with protein, and not as a result of a competing chemical or physical interaction, such as a pH change or preferential interaction with a test sample component other than protein. Moreover, it would be advantageous if the protein assay method is suitable for use both in wet assays and in dry reagent strips for the rapid, economical and accurate determination of protein in urine or other test samples. Additionally, the method and composition utilized in the assay for protein should not adversely affect or interfere with the other test reagent pads that are present on multiple test pad strips.

Prior to the present invention, no known method of assaying urine or other test samples for proteins included a reagent composition that provides sufficient sensitivity and color resolution of the assay at low to trace protein concentration levels, such that accurate and trustworthy protein assays can be made for protein concentrations of about 30 mg/dL and below. In addition, although a dry phase chemistry test strip utilizing a single dye, such as tetrabromophenol blue or tetrachlorophenol-3,4,5,6-tetrabromosulfophthalein, has been used extensively for several years, no dry phase test strip has incorporated a tungstate-dye complex to provide sufficient sensitivity, and therefore sufficient visual color-resolution between protein levels at low to trace protein concentration levels.

The prior art contains numerous references on the wet phase and the dry phase chemistry utilized in the pH indicator dye method of assaying urine for proteins. For example, Keston U.S. Pat. No. 3,485,587 discloses the basic dye binding technique used to assay for proteins at a constant pH. Keston teaches utilizing a single indicator dye, maintained at a constant pH slightly below the $pK_a$ (acid dissociation constant) of the dye, to determine the presence and/or concentration of albumin by monitoring the color transition of the dye.

The publication "Color Reaction Between Pyrogallol Red-Molybdenum (VI) Complex and Protein", Y. Fujita, I. Mori, and S. Kitano, *Bunseki Kagaku*, 32, pp. E379-E386 (1983), describes the protein interaction with a pyrogallol red-molybdenum complex requiring incorporation of a chelating agent or metal ion into the complex in order to determine protein concentrations.

Similarly, Japanese Patent No. 61/155757 (1986) discloses a colorimetric method of assaying for trace amounts of proteins in a test sample by using a composition including a molybdenum-dye complex and either a chelating agent or certain metal ions. However, it has been found that the method disclosed in Japanese Patent No. 61/155757 suffers from a severe ionic strength and specific gravity interference such that the extent of molybdate-dye binding to the protein, and therefore the degree of color transition, is inversely related to the ionic strength of the sample. Therefore, the assay of a urine sample of low ionic strength (low specific gravity) produces a greater color transition in the test device (therefore indicating a greater protein content) than the assay of a urine sample having the same protein content, but a higher ionic strength (higher specific gravity). Unexpectedly, the tungstate-dye complex utilized in the present invention does not suffer from an ionic strength/specific gravity interference and provides accurate protein assays regardless of test sample ionic strength Furthermore, it has been found that the inclusion of a chelating agent, added to the composition disclosed in the Japanese patent to suppress the blank reaction, is unnecessary and actually is detrimental to the method of the present invention.

The method disclosed in Japanese Patent No. 61/155757 also was described in the publication, "Urinary Protein as Measured with a Pyrogallol Red-Molybdate Complex, Manually and in a Hitachi 726 Automated Analyzer", N. Watanabe, S. Kamei, a. Ohkubo, M. Yamanaka, S. Ohsawa, K. Makino and K. Tokuda, *Clin. Chem.*, 32/8, pages 1551-1554 (1986). This publication describes the automated or manual detection of proteins in urine using the molybdate-dye complex. In addition to the disadvantages described above, the publication further reports that the interaction of interest between the protein and the molybdate-dye complex continued for at least eight minutes and is complete within 10 minutes at 37° C. for automated assays, but for manual assays, the interaction was allowed to continue for 20 minutes before the assay was examined for a response. Such a long interaction-time for the complete color transition to occur is both inconvenient and can lead to erroneous assays should the degree of color transition, and hence protein content, be determined too quickly. However, according to the method of the present invention, the interaction between the protein and the tungstate-dye complex is complete in less than two minutes, therefore providing faster results with a greatly reduced probability of an erroneous assay.

In contrast to the prior art, and in contrast to the presently available commercial test strips, the method of the present invention provides increased sensitivity in the detection and measurement of proteins in urine, especially low to trace amounts of proteins, by utilizing a reagent composition including a tungstate-dye complex, such that accurate assay for protein levels of about 30 mg/dL and below is achieved. Unexpectedly and surprisingly, the method of the present invention, also in contrast to the prior art, also allows the simple and fast detection and measurement of low to trace levels of protein in a liquid test sample. Hence, in accordance with the method of the present invention, new and unexpected results are achieved in the dry phase reagent strip assay and in the wet assay of urine and other test samples for proteins, especially for low to trace concentrations of proteins, by utilizing a reagent composition including a tungstate-dye complex.

SUMMARY OF THE INVENTION

In brief, the present invention is directed to a new and improved method and composition for determining the presence and/or concentration of a component in a test sample, especially low to trace amounts of the component. The method includes using a reagent composition capable of interacting with a test sample component to produce a detectable response. For home use, the reagent composition produces a visually detectable response For laboratory use, the reagent composition produces a response that is detectable visually or by instrument. The method is suitable for wet assays or for dry assays, wherein the reagent composition is incorporated into a carrier matrix of an analyte detection device. The carrier matrix of the analyte detection device comprises such bibulous porous materials as filter paper, or such nonbibulous porous materials as a permeable strip, layer or membrane of a polymeric material. A reagent composition is homogeneously incorporated into the carrier matrix, and the carrier matrix then holds the reagent composition homogeneously throughout the carrier matrix in a known concentration while maintaining carrier matrix penetrability for the liquid test sample.

More particularly, the present invention is directed to a method of assaying urine or other test samples for proteins, especially low to trace quantities of proteins, by utilizing a new and improved reagent composition. It has been demonstrated that employing a reagent composition including a tungstate-dye complex that affords sufficiently increased sensitivity and sufficient color resolution at low protein concentrations to permit the detection and measurement of low to trace protein concentrations in a liquid test sample. In accordance with an important feature of the present invention, the qualitative and/or semiquantitative determination of protein levels between 0 mg/dL and about 2000 mg/dL, and especially between 0 mg/dL and about 30 mg/dL, in urine and other test samples is accomplished By utilizing the tungstate-dye complex reagent composition of the present invention in clinical test methods, the qualitative and/or semiquantitative concentration of proteins, such as albumin, in urine or other test samples can be more accurately determined because the improved sensitivity of the method and the improved color resolution at low to trace concentrations of protein is achieved by the tungstate-dye complex reagent composition. Furthermore, surprisingly and unexpectedly, the tungstate-dye complex reagent composition incorporated into the analyte detection device allows the detection and measurement of low to trace protein concentrations, such as between 0 mg/dL and about 10 mg/dL, and also between 0 mg/dL and about 5 mg/dL and between about 5 mg/dL and about 10 mg/dL, in urine and other test samples.

Therefore, it is an object of the present invention to provide a new and improved method and composition for determining the relative concentration of a chemical compound in a liquid.

Another object of the present invention is to provide a simple, trustworthy, accurate and reproducible method of assaying urine or other test samples for proteins.

Another object of the present invention is to provide a simple,-trustworthy, accurate and reproducible method of assaying urine or other test samples for low concentrations and trace levels of proteins.

Another object of the present invention is to provide a new and improved protein interactive test device for interaction with protein in a test fluid to produce a visible change, such as a change in color, of the test device, indicative of the protein concentration in the test fluid.

Another object of the present invention is to provide a method of assaying urine or other liquid test samples that provides sufficient sensitivity and sufficient visual color resolution to allow the detection and measurement of low to trace protein concentrations.

Yet another object of the present invention is to provide a method of assaying urine or other liquid test samples that is sensitive to protein concentrations of less than about 10 mg/dL and that semiquantitatively discriminates between protein levels of from 0 mg/dL to about 2000 mg/dL, and especially from 0 mg/dL to about 30 mg/dL.

Another object of the present invention is to provide a method of assaying urine or other test liquids that utilizes an indicator reagent composition.

Another object of the present invention is to provide a method of assaying urine or other test liquids by utilizing an indicator reagent composition that can interact with proteins and undergo a detectable and measurable color transition to establish the presence and concentration of protein in the test sample.

Another object of the present invention is to provide an indicator reagent composition that can interact with proteins and undergo a visually and/or instrumentally differentiable color transition to allow the semiquantitative determination of the concentration of protein in the urine or other liquid samples at levels between 0 mg/dL and about 2000 mg/dL, and especially between 0 mg/dL and about 30 mg/dL.

Another object of the present invention is to provide a method of assaying for protein by incorporating an indicator reagent composition, including a tungstate-dye complex, into a dry phase analyte detection device.

Still another object of the present invention is to provide a new and improved method of assaying for protein by utilizing an analyte test device including a carrier matrix having incorporated therein a reagent composition capable of interacting with the protein content in a test sample, wherein the carrier matrix comprises a bibulous matrix like filter paper or a nonbibulous matrix, like a layer, film or membrane of permeable polymeric material.

A still further object of the present invention is to provide a new and improved dry phase test strip capable of incorporating a tungstate-dye complex reagent composition into the carrier matrix to achieve a test strip of new and unexpected precision in protein response.

The above and other objects and advantages and novel features of the present invention will become apparent from the following detailed description of the invention.

DETAILED DESCRIPTION OF THE INVENTION

In accordance with the method of the present invention, the qualitative and/or semiquantitative assay for proteins, such as albumin, and especially for low to trace concentrations of proteins, in urine and other liquid test samples is accomplished by utilizing an indicator reagent composition including a tungstate-dye complex. By employing an indicator reagent composition including a tungstate-dye complex, sufficient sensitivity to proteins and sufficient visual color resolution between protein levels is achieved to permit the assay of low to trace concentration levels of proteins in liquid test samples. The improved sensitivity and color resolution to low protein levels afforded by the method of the present invention is especially useful in urine assays.

Present-day commercial assays are incapable of differentiating between protein levels ranging from 0 mg/dL to about 30 mg/dL, and especially from 0 mg/dL to about 15 mg/dL. Differentiating between low protein concentration levels is clinically important in the art because a range of from about 10 mg/dL to about 20 mg/dL is used as the normal urine protein level for a healthy individual, therefore urine protein levels from 0 mg/dL to about 10 mg/dL may indicate a potential protein deficiency that can cause physiological imbalances and urine protein levels greater than about 20 mg/dL may indicate an excessive excretion of proteins that can signify a diseased state. It should be noted that in regard to urine protein concentrations in the relatively high range, such as from about 100 mg/dL to about 2000 mg/dL, the method of the present invention still affords improved sensitivity and color resolution to urine protein concentration, however such clinical benefits are less critical in this concentration range since such high protein levels are definitely indicative of an abnormal physiological state that must be investigated further.

Furthermore, it will become apparent that in addition to assaying urine, the method and composition of the present invention also can be used to determine the presence and semiquantitive concentration of albumin in blood plasma and serums; and more generally, the albumin content of many other albumin-containing fluids as well. In accordance with another important feature of the present invention, the method and composition of the present invention can be employed both in aqueous, liquid phase assays and, to achieve the full advantage of the present invention, in dry phase, test pad assays to determine the presence and/or concentration of proteins, especially low to trace concentrations of proteins, in urine or other liquid test samples.

Surprisingly and unexpectedly, it has been found that a reagent composition including a tungstate-dye complex demonstrated improved and increased sensitivity and visual color resolution to low to trace protein concentrations when used in a dye-binding technique to determine the presence and/or concentration of proteins in a test sample. The dye-binding technique using the tungstate-dye complex reagent composition provides a more accurate, trustworthy and clinically significant semiquantitative assay especially for low to trace concentrations of protein.

The dyes presently used in assays for protein interact with proteins and undergo a color transition due to the protein-error phenomena when maintained at the proper, constant pH. The protein-error phenomena is fully described in Keston U.S. Pat. No. 3,485,587, wherein the various dyes, the correct pH ranges and the buffers required to observe the protein-error phenomena are disclosed. The Keston patent basically describes the present day dry phase test strips employed to assay for total protein content in urine. These total protein test strips generally include an indicator dye that normally undergoes a color transition at a strongly acidic pH of 5 or below, and a buffer to maintain the pH of the indicator dye slightly below the pH of color transition for the dye. A sufficient buffering of the indicator dye essentially assures that the dye changes color due to an interaction with protein rather than due to a pH change occurring upon contact with the test sample.

Japanese Patent No. 61/155757 (1986) describes the use of a molybdate-dye complex and either a chelating agent or a certain metal ion to assay for protein in liquid samples. However, as discussed above, the Japanese method suffers from a serious ionic strength/specific gravity interference such that liquid samples having the same protein content but different ionic strengths/specific gravities will yield different protein assays. However, in accordance with an important feature of the present invention, it has been demonstrated that the ionic strength/specific gravity interference is overcome by using a tungstate-dye complex as the indicator component of the reagent composition. Surprisingly and unexpectedly, the tungstate-dye complex provides a more accurate and trustworthy assay for the total protein content in liquid samples than molybdate-dye complex method disclosed in the Japanese patent. In addition to more reliable protein assays, the tungstate-dye complex method of the present invention provides assay results four to five times faster than the molybdate-dye complex method. Therefore, a method of fast, accurate, reproducible and trustworthy protein assays, performable at home or in the laboratory to yield essentially immediate protein assay results, even for low to trace concentrations of proteins, is achieved.

In order to achieve the benefits afforded by the present invention, it is imperative that the indicator reagent composition includes a tungstate-dye complex as the indicator dye. In contrast both to the prior art and to presently available commercial assays, the incorporation of a tungstate-dye complex as the indicator compound of the reagent composition improves the color resolution and differentiation, both visually and instrumentally, of the color transition occurring upon interaction of the indicator with proteins. Therefore, the sensitivity of the protein assay, especially to low to trace protein concentrations, is increased.

The method of the present invention utilizes the "protein-error" phenomena previously discussed. However, the incorporation of a tungstate-dye complex as the indicator dyes of the reagent composition allows low to trace concentrations of protein to be detected and measured. As previously described, when a pH indicator dye interacts with a protein, the apparent $pK_a$ of the dye is altered and a color transition occurs producing the so-called "protein-error" phenomenon. Likewise, in accordance with an important feature of the present invention, the tungstate-dye complex similarly interacts with the protein content of the test sample and a more spectacular color development is achieved, therefore improving assay sensitivity and color resolution and differentiation upon interaction with proteins and accordingly permitting the measurement and detection of lower protein concentrations.

In general, the indicator component of the reagent composition utilized in the method of the present invention is a complex formed as a result of an interaction between a tungstate and a dye compound. It is of primary importance that the tungstate-dye complex is capable of interacting with proteins and undergoing a detectable and measurable color transition in response to the protein interaction. The tungstate-dye complex utilized in the indicator reagent composition must preferentially interact with proteins as opposed to any competing chemical or physical interactions with non-protein components in the test sample. Any appreciable competing interactions with non-protein components could lead to false and erroneous assays concerning the presence and amount of protein in the test sample. For example, the proper pH adjustment and buffering of the indicator reagent composition precludes the possibility of a color transition occurring because of a pH change in all cases except those wherein the test sample is sufficiently alkaline to overcome the affect of the buffers. In accordance with the method of the present invention, the pH of the tungstate-dye complex is adjusted to and is buffered at a pH value slightly below the pH range wherein the tungstate-dye complex changes color in order for the tungstate-dye complex to undergo its maximum color transition, and therefore most substantially increase assay sensitivity and most appreciably improve color resolution. Therefore, low to trace concentrations of proteins in the test sample are more readily and accurately assayed.

Furthermore, the dye employed in the tungstate-dye complex of the indicator reagent composition must undergo a sufficiently intense color transition such that relatively low concentrations of protein in the test sample will produce a detectable and measurable color transition. For example, the benefits of improved color resolution and increased assay sensitivity can be defeated or minimized if the tungstate-dye complex undergoes an insufficient color transition from a less intense color to a more intense color. Therefore, in order to achieve the full advantage of the present invention, the dyes employed in the tungstate-dye complex of the indicator reagent composition are selected such that the dye undergoes a sufficient color change either from a more intense color to a less intense color, or from a less intense color to a more intense color, such that the assayer, either visually or by instrument, can detect and measure the protein content of the test sample.

It has been found that the dye of the tungstate-dye complex used most advantageously in the method of the present invention is a polyhydroxybenzenesulfonephthalein-type dye, having a structure similar to the dyes pyrocatechol violet and pyrogallol red, illustrated below in structural formulas I and II, respectively.

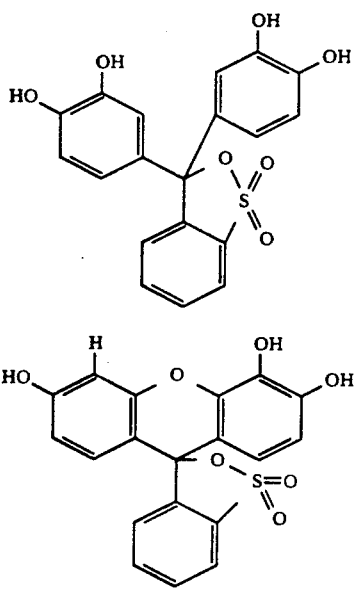

Suitable dyes having the polyhydroxy-substituted benzenes and a sulfonephthalein-type structure in addition to pyrocatechol violet and pyrogallol red include bromopyrogallol red, xylenol orange and pyrogallol phthalein; and mixtures thereof. Similarly, the polyhydroxybenzenephthalein-type indicators, such as pyrogallolphthalein, depicted in structure formula III, and o-hydroxyhydroquinonphthalein also can be used in the method and composition of the present invention.

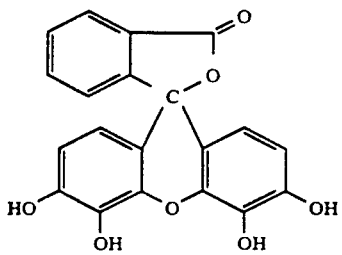

These polyhydroxybenzenesulfonephthalein-type dyes and polyhydroxybenzenephthalein-type dyes can complex to metal oxides, such as tungstates; can bind to proteins after complexing with a metal oxide; and can undergo a sufficient color transition after complexing and then binding to a protein to allow the visual and/or instrumental detection and/or measurement of the protein content of a test sample, including low to trace concentrations of protein in the sample. Depending upon several chemical and physical parameters, such as ability to interact with proteins, color of the test sample, intensity of the color transition and chemical compatibilities, a particular polyhydroxybenzenesulfonephthalein-type dye, or polyhydroxybenzenephthalein-type dye, is selected for complexing with the tungstate to form the indicator component of the reagent composition. The exact polyhydroxybenzenesulfonephthalein-type dye, or polyhydroxybenzenephthalein-type dye, selected as the dye compound of the tungstate-dye complex component of the indicator reagent composition can be determined by those skilled in the art of designing test kits in order to produce an assay for proteins having maximum visual color resolution and maximum sensitivity. The polyhydroxybenzenesulfonephthalein-type dyes and polyhydroxybenzenephthalein-type dye utilized in the tungstate-dye complex compound of the indicator reagent composition of the present invention can be prepared by methods well known to persons in the art. Furthermore, several dye compounds that are useful in the method of the present invention are well known indicator dyes that are presently available commercially.

In accordance with another important feature of the present invention, the polyhydroxybenzenesulfonephthalein-type dye or polyhydroxybenzenephthalein-type dye must be combined with a tungstate salt to produce the tungstate-dye complex indicator component of the reagent composition. Japanese Patent 61/155757 described a protein assay employing a molybdenum-dye complex that also used a polyhydroxybenzenesulfonephthalein-type dye, however using a molybdate salt required a chelating agent or a metal ion to be present in the composition to suppress the blank reaction In addition, the accuracy of the Japanese method is suspect because of interferences resulting from variances in the ionic strength and the specific gravity of the test sample. The molybdate method also requires abnormally long contact times for full color development of the test device. Surprisingly and unexpectedly, using a tungstate salt avoids the problem of test sample ionic strength and specific gravity interference, dramatically shortens the time required for full color development of the test device, and does not require, and actually cannot tolerate, the presence of a chelating agent or metal ion to suppress the blank reaction.

The particular tungstate salt utilized in the tungstate-salt complex is not particularly limited. However, the tungstate salt must have sufficient water solubility such that the tungstate salt can be solubilized for complexing with the polyhydroxybenzenesulfonephthalein-type or polyhydroxybenzenephthalein-type dye. Furthermore, it is preferred that the cation of the tungstate salt utilized in the present invention is essentially colorless in order to avoid assay interference due to a highly colored cation. Tungstate salts exhibiting sufficient water solubility to allow complexing with the polyhydroxybenzenesulfonephthalein-type or polyhydroxybenzenephthalein-type dye include, but are not limited to, ammonium tungstate, ammonium paratungstate, bismuth tungstate, cadmium tungstate, calcium tungstate, lithium tungstate, magnesium tungstate, potassium tungstate, sodium metatungstate, sodium tungstate, strontium tungstate, zinc tungstate, phosphotungstates having an alkali metal and/or an ammonium and/or an alkyl, dialkyl, trialkyl or tetraalkylammonium cation, alkylammonium or hydroxyalkylammonium tungstates, dialkylammonium or di(hydroxyalkyl)ammonium tungstates, and trialkylammonium or tri(hydroxyalkyl)ammonium tungstates; or combinations thereof.

In accordance with an important feature of the present invention, the preferred tungstate salts used to complex with the polyhydroxybenzenesulfonephthalein-type or polyhydroxybenzenephthalein-type dye are the highly water-soluble tungstate salts and those tungstates salts including non-complexing and non-interfering metal and ammonium cations. To achieve the full advantage of the present invention, ammonium tungstate, potassium tungstate, sodium tungstate, lithium tungstate, strontium tungstate, and the alkyl-or hydroxyalkyl-substituted ammonium tungstates, or combinations thereof are used as the tungstate salt to produce the tungstate-dye complex of the present invention.

A complex of a polyhydroxybenzenesulfonephthalein-type or polyhydroxybenzenephthalein-type dye and a suitable tungstate salt is utilized as the indicator component of a reagent composition in an improved method to determine the presence and/or the semiquantitative concentration of protein, and especially low to trace concentrations of protein, in urine or other liquid test samples. It has been demonstrated that the indicator reagent composition of the present invention interacts with proteins to produce a differentiable and measurable color transition, either visually and/or by instrument, due to the "protein-error" phenomena. However, in addition to the tungstate-dye complex, the indicator reagent composition of the present invention may require a sufficient amount of a proper buffer, such that the tungstate-dye complex will not change color as a result of a pH shift, but will change color upon contact and interaction with proteins to accurately establish the presence and/or semiquantitative concentration of protein in the test sample.

Further, it has been demonstrated that any of various known types of buffers can be used in the indicator reagent composition of the present invention. The function of the buffer is to maintain the reagent system at a substantially constant pH to produce the desired color transition in the indicator reagent composition because of the presence of proteins and to essentially eliminate color changes due to a variation in the pH of the protein-containing test sample. As a result, the amount of buffer incorporated into the reagent composition depends upon the nature of the test sample. The quantity of buffer usually falls between about 100 millimolar (mM) and about 500 millimolar (mM), although in particular cases the amount of buffer can be above or below this range. The nature of the buffer used will depend upon, and vary with, the tungstate-dye complex incorporated into the indicator reagent composition. However, it has been found that for optimum results, the pH of the reagent composition generally should be maintained at a pH value only slightly below the pH range wherein the tungstate-dye complex of the reagent composition undergoes a color transition, normally in the pH range of approximately 2 to approximately 4, and preferably in the range of approximately 2 to approximately 3. A method of determining a suitable buffered pH value for the particular indicator dyes of the reagent composition and of determining the particular buffer than can be used in the dual indicator reagent composition is found in Keston, U.S. Pat. No. 3,485,587.

Although the use of a buffer in the present reagent composition is preferred, a buffer is not essential in all cases. For example, in special cases it may be desirable to add a buffer to the urine or other test sample before the test sample contacts the reagent composition. Also the test sample may already contain a buffer of the proper type and in the proper amount to maintain the reagent composition at a constant pH, or the tungstate-dye complex reagent composition may be insensitive to pH changes. In such cases, the tungstate-dye complex can be the sole active ingredient in the indicator reagent composition. However, it should be understood that optional ingredients, such as surfactants, that do not materially alter the nature and the function of the indicator tungstate-dye complex and/or the buffer and that do not interfere with the protein assay, also can be included in the indicator reagent composition. Likewise, other such non-essential ingredients include polymeric compounds, plasticizers and non-active background dyes.

Upon contact with the urine or other test sample, a color transition of the tungstate-dye complex indicator reagent composition demonstrates the presence of protein. Furthermore, the intensity and degree of the color transition can be used to determine the semiquantitative concentration of protein in the test sample by comparing or correlating the color produced by the test sample to colors produced by solutions having a known concentration of protein. In accordance with an important feature of the present invention, it has been demonstrated that the indicator reagent composition provides a sufficiently resolved and differentiated color transition such that the amount of protein, including low to trace amounts of protein, in the test sample can be measured and accurately determined without the use of color-measuring instruments, such as spectrophotometers or colorimeters. However, if desired, such color-measuring instruments can be used to measure the difference in color degree and intensity between the test sample and a solution of known albumin concentration.

Accordingly, an assay for protein that utilizes a suitably buffered indicator reagent composition including a tungstate-dye complex improves the accuracy and reliability of the assay and also increases physician confidence in the assay. Additionally, because of the number of urine assays for protein being performed at home by the untrained patient, as opposed to trained physicians or technicians in the laboratory, it is imperative to provide accurate and reliable semiquantitative have assay methods for protein content, including low to trace protein content in the urine.

In general, assays for protein have been conducted at an acidic pH and using an indicator dye undergoing a color transition at an acidic pH because the indicator dye can interact more strongly with the protein at low, acidic pH values. The increased interaction between the indicator dye and the protein at low pH values occurs because of a strong attraction between the positively-charged cationic protein molecule and the negatively-charged anionic indicator dye molecule, and, additionally, because the acidic conditions serve to partially denature proteins and therefore increase the ability of the protein to interact with the indicator dye. Therefore, the tungstate-dye complex of the indicator reagent composition is adjusted to and maintained at an acidic pH. Generally, the pH of the system is adjusted to and maintained at between about 2.0 and about 4.0; and to achieve the full advantage of the present invention the pH is adjusted to and maintained at between about 2.5 and 3.5.

To demonstrate the new and unexpected results achieved by the-method and composition of the present invention, an indicator reagent composition, including a complex formed between ammonium tungstate and the polyhydroxybenzenesulfonephthalein-type dye, pyrocatechol violet, was prepared, then used in an aqueous, liquid phase assay for total protein content of a test sample. The tungstate-pyrocatechol violet complex interacts with proteins and undergo a color transition at a pH of approximately 2.5. An aqueous solution of the tungstate-pyrocatechol violet complex is dark purple-brown in color in the absence of proteins and changes color ranging from reddish brown to yellow to light green to green to deep blue in the presence of increasing amounts of proteins. As a result, an indicator reagent composition including the appropriate amounts of a tungstate, like ammonium tungstate, and pyrocatechol violet, adjusted to and maintained at a suitable pH with a suitable buffer produced the color transitions summarized in TABLE I upon contact with standardized protein solutions. The color transitions summarized in TABLE I show that a test sample containing 5 mg/dL of albumin can be differentiated from a test sample containing 0 mg/dL and from a test sample containing 10 mg/dL. These color differentiations are more dramatic as the concentration of the dye-tungstate complex in the indicator reagent composition is increased. Therefore, in accordance with the present invention, a composition and method of measuring low to trace protein levels in a test sample and of differentiating between test samples having almost identical albumin concentrations is achieved.

TABLE I

COLOR TRANSITION OF AMMONIUM TUNGSTATE-PYROCATECHOL VIOLET COMPLEX INDICATOR REAGENT COMPOSITION UPON INTERACTION WITH STANDARDIZED PROTEIN SOLUTIONS (pH = 2.5)

| Concentration of Standardized Protein Solution (mg/dL) | Observed Color |
| --- | --- |
| 0 (blank - negative) | Dark purple brown |
| 5 | Dark reddish brown |
| 10 (trace - low) | Light reddish brown |
| 20 (low) | Yellowish brown |
| 30 | Light green |
| 100 | Green |
| 300 | Dark Blue |

In accordance with an important feature of the present invention, the improved color resolution achieved by using the tungstate-pyrocatechol violet complex indicator reagent composition permits detection and differentiation between protein concentrations of 0, 5, 10, 20 and 30 mg/dL. In contrast, all prior art methods employing an indicator dye are unable to differentiate between protein levels in the 0 to about 15 mg/dL range and provide only minimal differentiation between protein levels ranging from 0 to about 30 mg/dL. However, in accordance with the present invention, increased assay sensitivity is achieved, especially at test sample protein levels of about 30 mg/dL and below, to ultimately yield more accurate and meaningful assay results.

To perform an aqueous, liquid phase assay for total protein content, the tungstate-dye complex indicator reagent composition is produced first. For example, a tungstate-dye complex indicator reagent composition is produced by dissolving 0.010 g (.026 millimole) of pyrocatechol violet, 0.024 g (.085 millimole) of ammonium tungstate and 0.75 g of glycine in a sufficient amount of (approximately 70 to 80 mL (milliliter)) of distilled water. The pH of the resulting solution is titrated with an aqueous solution of hydrogen chloride (HCl) to adjust the pH to 2.5. The pH adjusted solution is transferred to a 100 mL volumetric flask, and the total volume is adjusted to 100 mL with distilled water. The final solution includes a 0.3 mM (millimolar) concentration of pyrocatechol violet and 0.8 mM concentration of tungstate. The 0.75 g of glycine was added to the indicator reagent composition to serve as a buffer. The presence and concentration of protein in a urine sample then was determined by adding one drop (approximately 50uL (microliters)) of urine to one ml of the tungstate-pyrocatechol violet complex indicator reagent composition. The color of the resulting aqueous solution changed from dark purple-brown through yellow to green, therefore revealing the presence of approximately 100 mg/dL of protein in the urine sample.

It should be noted that no chelating agents, such as tartaric acid or oxalic acid, are included in the tungstate-dye complex indicator reagent composition. It has been demonstrated that the presence of a chelating agent in the tungstate-dye complex reagent composition effectively destroys the ability of the reagent composition to detect albumin. However, suprisingly and unexpectedly, in the absence of a chelating agent, the tungstate-dye complex indicator reagent composition undergoes a spectacular color transition upon contact and interaction with proteins. This spectacular color development is unexpected in that Japanese patent 61/155757, describing the molybdate reagent, required a chelating agent in order to produce a color change upon molybdate-dye complex contact and interaction with proteins.

In general, in the aqueous, liquid phase assay for protein, the tungstate-dye complex indicator reagent composition is present in a sufficient amount to allow the visual and/or instrumental detection and measurement of a color transition. However, an excess amount of tungstate-dye complex indicator reagent composition should be avoided such that any non-specific interactions with non-protein test sample components are essentially precluded. Usually, a total concentration of the tungstate-dye complex in the indicator reagent composition in the range of about 0.3 millimolar (mM) to about 5 mM is sufficient to provide a detectable and differentiable color transition, either visually and/or by instrument, even for low to trace amounts of protein in the test sample, and to eliminate or minimize assay interference through tungstate-dye complex interaction with non-protein test sample components. To achieve the full advantage of the present invention, it has been found that a total tungstate-dye complex concentration in the indicator reagent composition in the range of from about 1 mM to about 4 mM is especially preferred. In addition, it also has been found that assay sensitivity to low to trace protein levels, such as 5 mg/dL, is further increased as the concentration of the tungstate-dye complex indicator reagent composition in the liquid phase assay is increased from about 1 mM up to about 4 mM.

Furthermore, it also has been found that in addition to the glycine buffer used in the above example, the desired pH can be maintained at an essentially constant level by using any suitable buffer that does not contain a chelating anion, such as lactate, phthalate, trichloroacetate, sulfosalicylate, phosphates, acetates, sodium chloride/hydrochloric acid, piperazine-N,N'-bis(2-hydroxypropane)sulfonic acid (POPSO), N-2-hydroxyethyl-piperazine-N'-2-ethanesulfonic acid (HEPES), 3-N-(tris-hydroxymethyl)methylamino-2-hydroxypropanesulfonic acid (TAPSO), 2-([tris-(hydroxymethyl)-methyl]-amino)ethanesulfonic acid (TES), or other suitable buffers as are well known in the art.

Additionally, the particular tungstate and the particular polyhydroxybenzenesulfonephthalein-type or polyhydroxybenzenephthalein-type dye included in the indicator reagent composition do not necessarily have to be present in the approximately 1 to 3.25 molar ratio of dye to tungstate present in the preceding example. As will be discussed more fully hereinafter, by increasing the concentration of both the tungstate and the particular polyhydroxybenzenesulfonephthalein-type or polyhydroxybenzenephthalein-type dye in the indicator reagent composition, the protein assay is more sensitive to low to trace amounts of proteins in the test sample. It has been found that increasing the ammonium tungstate concentration to 0.03 g/dL (grams per deciliter), or 0.078 millimole, and increasing the concentration of the pyrocatechol violet to 0.075 g/dL, or 0.255 millimole, or a molar ratio of dye to tungstate of approximately 1 to 3.25, provides improved color-differentiation between test samples containing low to trace amounts of protein. It also has been found that a molar ratio of the dye to the tungstate within a range of from about 1 to 1 to about 1 to 10, and preferably in the range of from about 1 to 2 to about 1 to 5, provides the full advantages and benefits of the present invention. In addition, it has been found that, if the molar ratio is held constant, by increasing the concentration of the dye and the tungstate salt in the indicator reagent composition, improved color differentiation between test samples having a low to trace concentration of protein is achieved.

Furthermore, in accordance with another important feature of the present invention, it is well within the experimental techniques of those skilled in the art of preparing test devices to design a system for the aqueous semiquantitative assay of proteins in urine and other liquid samples by varying the relative amounts of aqueous solvent, tungstate-dye indicator reagent composition, and urine sample, and by varying the identity and amount of tungstate-dye complex and buffer, to provide detectable and differentiable color transitions, such that a comparison, either visually and/or by instrument, to color standards derived from solutions of known protein concentration is possible.

In addition to the wet phase, aqueous assay for proteins, the tungstate-dye complex indicator reagent composition can be used in dry phase, test pad assay for protein that utilizes the tungstate-dye indicator reagent composition is performed in accordance with methods well known in the art. In general, the assay for protein is performed by contacting the urine or other test sample with an analyte detection device that includes the tungstate-dye indicator reagent composition. The analyte detection device can be dipped into the test sample, or the test sample can be applied to the analyte detection device dropwise. The resulting change in color of the analyte detection device demonstrates the presence of protein; and, if so designed, the resulting color transition can be compared to a standardized color chart to provide a semiquantitative measurement of the concentration of protein in the urine or test sample.

Typically, the analyte detection device is a reagent composition impregnated test strip, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move, in response to capillary forces, through the matrix to contact the reagent composition and produce a detectable and measurable color transition.

The carrier matrix can be any substance capable of incorporating the chemical reagents required to perform the assay of interest, as long as the carrier matrix is substantially inert with respect to the chemical reagents and does not contaminate the urine or other test samples either by test sample extraction of components comprising the carrier matrix or by appreciably altering the urine or test sample in a way to make the subsequent assays inconclusive, inaccurate or doubtful. The carrier matrix also must be porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occuring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and non-absorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix must include a hydrophilic or absorptive material. The handle usually is formed from hydrophobic materials such as cellulose acetate, polyethylene, terephthalate, polycarbonate or polystyrene, and the carrier matrix is most advantageously constructed from bibulous filter paper or nonbibulous permeable polymeric films.

To achieve the full advantage of the present invention, the tungstate-dye complex indicator reagent composition is impregnated into a suitable carrier matrix and utilized in a dry phase test strip for the assay of protein in a test sample. The method of the present invention affords an economical, accurate and reliable assay for the total concentration of protein in test samples that can be performed at home or in the laboratory. In addition, the method of the present invention allows detection, differentiation and measurement of low to trace protein concentrations in the test sample therefore making the assay more useful clinically.

In accordance with the method of the present invention, to perform a dry phase, test strip assay for protein, an aqueous solution, including from about 0.3 millimolar (mM) to about 5 mM total concentration of a tungstate-dye indicator, such as tungstate-pyrocatechol violet indicator, adjusted to and buffered at a pH of 2.5, first is prepared. A bibulous matrix, such as filter paper, like WHATMAN CCP500 filter paper, available commercially from Whatman Ltd., Maidstone, Kent, U.K., then is saturated and impregnated with the aqueous solution containing the tungstate-dye indicator reagent composition either by spreading, by immersing or by spraying the aqueous solution onto sheets or precut strips of the filter paper. After removing the aqueous solvent by oven drying in an air oven at about 50° C. for about 15 to 20 minutes, the filter paper impregnated with the tungstate-dye complex indicator reagent composition is cut to an appropriate size, such as a pad having dimensions from about 0.25 cm by about 0.5 cm to about 0.5 cm by about 1.0 cm. The filter paper impregnated with the tungstate-dye complex indicator reagent composition then is secured to an opaque or transparent hydrophobic plastic handle with double sided adhesive tape.

The resulting test strip then was dipped into a fresh, uncentrifuged urine sample for a sufficient time to saturate the test pad with the sample. After waiting a predetermined time, such as from about 1 min. to about 2 min., the test strip is examined, either visually or by instrument, for a response. The color transition, if any, of the test pad reveals the presence and/or concentration of protein in the urine sample.

Analogous to the aqueous, liquid phase assay for protein described previously, it is well within the experimental techniques of those skilled in the art of preparing test devices to determine the proper balance between size of reagent pad, the strength of tungstate-dye complex indicator reagent impregnating solution, the amount of test sample, and the method of introducing the test sample to the test strip, such as by pipetting rather than dipping, in order to design a semiquantitative assay for protein utilizing the method and composition the present invention.

In many cases simple visual observation of the test strip provides the desired information. If more accurate information is required, a color chart bearing color spots corresponding to various known protein concentrations, can be prepared for the particular tungstate-dye complex indicator reagent composition used in the test strip. The resulting color of the test strip after contact with the urine sample then can be compared with the color spots on the chart to determine the protein concentration of the test sample.

If a still more accurate determination is required, a spectrophotometer or colorimeter can be used to more precisely determine the degree of color transition. In addition, both the aqueous, liquid phase assay and the dry phase, reagent strip assay can be made semiquantitative by employing spectrophotometric or colorimetric techniques, as opposed to visual techniques, in order to more reliably and more accurately measure the degree of color transition, and therefore more accurately measure the concentration of protein in the test sample, especially at lower protein concentrations, such as below 30 mg/dL, and especially below 15 mg/dL.

As will be discussed more fully hereinafter, the ability to detect, differentiate between and measure low to trace concentrations of proteins in a test sample by employing a tungstate-dye complex indicator reagent composition surprisingly and unexpectedly provides an improved method of assaying for the total protein content of liquid test samples. For example, according to present day methods, the accurate detection and measurement of protein concentrations in urine below about 30 mg/dL requires a heat and precipitation technique that is expensive and time-consuming. Accordingly, until the method of the present invention, no dry phase, test strip technique was available to accurately detect and measure the low to trace concentrations, such as below about 15 mg/dL, of protein often found in urine. Therefore, in accordance with an important feature of the present invention, it has been demonstrated that by impregnating the tungstate-dye complex indicator reagent composition into a suitable carrier matrix, the presence and concentration of low to trace concentrations of protein in a urine sample can be achieved by using a dry phase test strip.

To show the new and unexpected results arising from using the tungstate-dye complex indicator reagent composition to detect and measure the amount of protein in a test sample, color space plots were made from total protein assays using dry phase test strips including either a tungstate-dye complex indicator composition or a molybdate-dye complex indicator composition impregnated into a filter paper matrix. Color space plots were obtained by contacting standardized albumin solutions with various dry phase test strips comprising either a tungstate-dye complex indicator reagent composition or a molybdate-dye complex indicator reagent composition impregnated into a filter paper carrier matrix.

In general, a color space plot includes three axes, the $L^*$, $A^*$ and $B^*$ axes. The values of $L^*$ plotted on the vertical axis are a measure of the intensity of color, whereby a large $L^*$ value denotes a light color and $L^*=0$ denotes a completely black color. The horizontal $A^*$ axis is a measure of the color transition from green to red, whereby the more positive the $A^*$ value, the more red the color, and analogously, the more negative the $A^*$ value, the more green the color. Similarly, the third axis, $B^*$, is a measure of the color transition from blue to yellow, whereby the greater the value of $B^*$, the more yellow the color, and analogously the smaller the value of $B^*$, the more blue the color.

The color space difference ($\Delta E$) is calculated from the following equation (Eq. 1):

$$\Delta E = \sqrt{(L_1^* - L_2^*)^2 + (A_1^* - A_2^*)^2 + (B_1^* - B_2^*)^2} \qquad \text{Eq. 1}$$

wherein:

$L_1^*$, $A_1^*$, and $B_1^*$ are the color space values determined for a first standardized protein solution;

$L_2^*$, $A_2^*$ and $B_2^*$ are the color space values determined for a second standardized protein solution having a different protein concentration from the first standardized protein solution; and $\Delta E$ is the color space difference between the color space plots of the first and second standardized protein solutions.

The color space difference ($\Delta E$) is the straight line distance between two points in a three-dimensional color space plot. Theoretically, a color space difference of 1 is the smallest color difference the human eye can distinguish. However, because of the inherent differences between the visual capabilities of individuals, a color space difference ($\Delta E$) of about 5 is required in order to practically and confidently distinguish between colors.

The $L^*$, $A^*$ and $B^*$ values plotted on the color space plots are calculated from the percent reflectance measurements taken at sixteen different wavelengths evenly spaced between 400 nm (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values X, Y and Z, and L*, A* and B* are calculated from the X, Y and Z tristimulus values using the following equations:

$$L^* = 116 \times [(Y/Y_o)^{\frac{1}{3}} - 16)] \quad \text{(Eq. 2)}$$

$$A^* = 500 \times [(X/X_o)^{\frac{1}{3}} - (Y/Y_o)^{\frac{1}{3}}] \quad \text{(Eq. 3)}$$

$$B^* = 200 \times [(Y/Y_o)^{\frac{1}{3}} - (Z/Z_o)^{\frac{1}{3}}] \quad \text{(Eq. 4)}$$

wherein:

Xo, Yo and Zo are the tristimulus values for perfect white (i.e. reflectance = 100% at all wavelengths), and X, Y and Z are the tristimulus values calculated as described above from the sixteen wavelengths between 400 nm and 700 nm.

From the color space plots, the color space differences (ΔE) were calculated, and are summarized and discussed in more detail hereinafter. In interpreting the data to be presented, a term such as ΔE(Alb 15-0) is the color space difference between protein assays for standardized protein solution containing 15 mg/dL of albumin and 0 mg/dL of albumin. Similarly, the term ΔE-(Alb 30-0) is the color space difference between protein assays for protein solutions containing 30 mg/dL of protein and 0 mg/dL of protein. The term ΔE(Alb100-0) is analogously defined, wherein Alb refers to the protein albumin. Similarly, a term such as ΔE(1.0-07-1.0012) refers to the color space difference between protein assays for standardized urine solutions having the same protein concentration but having different specific gravities of 1.007 and 1.0012, and therefore, different ionic strengths.

Initially, to show the inherent disadvantages and drawbacks of using the prior art molybdate-dye complex to assay urine for protein content, TABLE II summarizes a series of assays on urine samples containing the same amount of the protein albumin but having differing ionic strengths and specific gravities due to the addition of sodium chloride.

TABLE II

DEPENDENCE OF PRIOR ART MOLYBDATE-DYE INDICATOR REAGENT SYSTEM UPON IONIC STRENGTH (SPECIFIC GRAVITY)

| Specific Gravity of Urine Containing No Albumin | Color Transition of Molybdate-Dye Indicator (Reagent A) | Color Transition of Tungstate-Dye Indicator (Reagent |
|---|---|---|
| 1.007 | Blue | Blue |
| 1.012 | Lt. Blue, and some gray | Blue |
| 1.020 | Gray, and some brown & yellow | Blue |
| 1.028 | Gray, and some brown & yellow | Blue |
| 1.032 | Gray, and some brown & yellow | Blue |

In Table II, the molybdate-dye indicator (reagent A) was prepared by adding 0.075 g of human albumin to a 25 ml volumetric flask, then filling the flask to a volume of 25 ml. with an ammonium molybdate-pyrocatechol violet-tartaric acid indicator solution, adjusted to and buffered at a pH of 2.5. This solution contains the equivalent of 300 mg/dL of albumin. The tungstate-dye indicator (reagent B) was prepared similarly, except the ammonium molybdate is replaced by ammonium tungstate, and the tartaric acid is omitted. Reagent A and reagent B were impregnated into separate pieces of WHATMAN CCP500 filter paper. The impregnated filter paper sections were dried and cut into strips, as described above. The test strips then were dipped briefly into urine samples, each containing no albumin, but with a different specific gravity and ionic strength due to the addition of sodium chloride. From the observations listed in TABLE II, it can be seen that the tungstate-dye indicator (reagent B) did not show a specific gravity/ionic strength dependence, while the molybdate-dye indicator (reagent A) changed color from blue to grayish brown upon an ionic strength increase and a specific gravity increase from 1.007 to 1.020 even though the albumin content in the test sample remained unchanged. A molybdate-dye indicator reagent including 400 mg/dL of albumin gave identical results as molybdate-dye reagent A, both in assays of samples containing 0 mg/dL protein and 15 mg/dL protein.

It should be noted that an identical companion series of tests was performed by preparing test strips as described above but omitting the human albumin. When these test strips were dipped briefly into urine samples each containing 0 mg/dL of albumin and each having a different ionic strength and specific gravity, the test strips gave results similar to those listed in TABLE II, except that the color of the low ionic strength/specific gravity sample was grayish red rather than blue. These tests thereby demonstrate that the test strips impregnated with the molybdate-dye indicator (reagent A) change color in response to ionic strength/specific gravity variations.

In addition, if the urine sample specific gravity is increased, but the ionic strength held constant, such as by the addition of glucose rather than sodium chloride to the urine sample, the color transition due to an increase in ionic strength does not occur, showing that the molybdate-dye indicator is more sensitive to the changes in ionic strength of the sample than to the specific gravity changes of the sample. As demonstrated above, and as will be discussed more fully hereinafter, surprisingly and unexpectedly, it was found that urine protein assays using test strips incorporating the tungstate-dye complex of the present invention into the indicator reagent composition are not influenced by the ionic strength, or the specific gravity, of the test sample.

To demonstrate the independence of the tungstate-dye complex indicator reagent composition from the effects of urine ionic strength and specific gravity, an indicator reagent test strip was made by dipping a filter paper carrier matrix into 100 ml of an aqueous, solution including 0.0102 g (0.026 millimole) of pyrocatechol violet, 0.0151 g (0.005 millimole) of ammonium tungstate, and 250 mM glycine adjusted to and buffered at a pH of 2.5. Test strips incorporating the tungstate-pyrocatechol dye complex indicator reagent composition were used to assay standardized urine samples containing 0 mg/dL, 15 mg/dL, 30 mg/dL and 100 mg/dL of albumin. For each albumin concentration, the specific gravity of a urine sample was adjusted to 1.007, 1.012, 1.020, 1.028 and 1.032 with sodium chloride or glucose. Color space plots were obtained, and the color space differences (ΔE) were calculated for each albumin concentration over the specific gravity range of 1.007 to 1.032. The results are outlined in TABLES III.

TABLE III

COLOR SPACE DIFFERENCES (ΔE) FOR PROTEIN ASSAYS USING THE TUNGSTATE-DYE COMPLEX INDICATOR REAGENT COMPOSITION IN RESPONSE TO SAMPLES OF SAME ALBUMIN CONTENT BUT DIFFERENT IONIC STRENGTHS (SPECIFIC GRAVITIES)

| Albumin Conc. | ΔE (1.007–1.0012) | ΔE (1.007–1.020) | ΔE (1.007–1.028) | ΔE (1.007–1.032) |
|---|---|---|---|---|
| 0 mg/dL | 1.90 | 2.64 | 3.01 | 3.19 |
| 15 mg/dL | 0.80 | 1.87 | 1.49 | 1.94 |
| 30 mg/dL | 1.13 | 1.73 | 2.26 | 2.56 |
| 100 mg/dL | 1.66 | 1.63 | 3.24 | 2.79 |

As demonstrated in TABLE III, the variance in the color space difference due to a change in the ionic strength (specific gravity) of the urine sample ranged from only 0.80 units to a maximum of 3.24 units, values that are sufficiently below the normally recognized minimum value of 5 units required for the human eye to detect a color change Overall, it has been demonstrated that the tungstate-dye complex indicator reagent composition is subject to little to no interference arising from the ionic strength or specific gravity of the test sample, because, from TABLE III, the maximum specific gravity effect is about 3 ΔE units. Such small color space difference values stand in direct contrast to the actual visually detectable color changes summarized in TABLE II for the molybdate-dye complex of the prior art in response to specific gravity (ionic strength) changes in the urine samples. It should be noted that adding glucose to increase the specific gravity of the urine sample gave a color space difference (ΔE) of 2.37 units for a urine specific gravity change of from 1.007 to 1.015, and a ΔE of 3.84 units for a urine specific gravity change of from 1.007 to 1.022 when a tungstate-dye complex indicator reagent composition is used as the indicator in a urine protein assay. Again these ΔE values are below the normal visually detectable limit of 5 units, therefore showing the independence of a protein assay using the tungstate-dye complex indicator reagent composition from the affects of specific gravity alone.

The results summarized in TABLE II for the molybdate-dye indicator reagent A are quantified in TABLE IV wherein color space plots were obtained for protein assays of urine samples having different albumin concentrations and different specific gravities and ionic strengths. It was found that varying the specific gravity of the urine sample by adding glucose did not affect the protein assays using the molybdate-dye complex method of the prior art because ΔE (1.007–1.015) is 2.24 units and ΔE (1.007–1.022) is 1.21 units, both below the minimum detectable level of about 5 units. However, TABLE IV shows that using sodium chloride to increase the specific gravity of the urine sample also increases the ionic strength of the urine sample, and as a result, unlike the method of the present invention, adverse affects on the protein assays are observed A careful examination of TABLE IV shows that the color space differences obtained for test samples having the same albumin content but differing ionic strengths and specific gravities generally exceeds 5 units, therefore showing that a visible color difference, and a potentially erroneous protein assay, will be detected by the human assayer.

TABLE IV

ΔE DIFFERENCES IN PROTEIN ASSAYS USING THE MOLYBDATE-DYE COMPLEX INDICATOR REAGENT BETWEEN TEST SAMPLES HAVING THE SAME ALBUMIN CONTENT AND DIFFERENT SPECIFIC GRAVITIES AND IONIC STRENGTHS

| Albumin Conc. | ΔE (1.007–1.0012) | ΔE (1.007–1.020) | ΔE (1.007–1.028) | ΔE (1.007–1.032) |
|---|---|---|---|---|
| 0 mg/dL | 6.41 | 12.08 | 15.43 | 17.08 |
| 15 mg/dL | 6.32 | 13.12 | 15.75 | 17.06 |
| 30 mg/dL | 5.74 | 12.73 | 15.79 | 16.72 |
| 100 mg/dL | 9.95 | 14.54 | 15.73 | 17.77 |

Surprisingly and unexpectedly, the results listed in TABLE IV for urine protein assays using the molybdate-dye complex described in the prior art are in direct contrast to the results listed in TABLE III for urine protein assays using the tungstate-dye complex indicator reagent composition of the present invention. A comparison of the data presented in TABLE III to the data presented in TABLE IV illustrates that the method of the present invention is free from assay interferences due to the ionic strength and specific gravity of the test sample. In TABLE III, using the tungstate-dye complex, the color space differences are all less than the generally recognized minimum detectable limit of 5 units. However, in TABLE IV, using the molybdate-dye complex, essentially all of the color space differences are well above the minimum detectable limit of 5 units, therefore giving a variable protein assay depending upon the specific gravity (ionic strength) of the test sample.

In accordance with another important feature of the present invention, it has been found that by increasing the amount of ammonium tungstate used to make the ammonium tungstatepyrocatechol violet complex indicator from the 0.0151 g ammonium tungstate used in all previous tests to 0.075 g ammonium tungstate and by increasing the amount of pyrocatechol violet from the 0.0105 g pyrocatechol violet to 0.03 g of pyrocatechol violet to produce 100 ml of the aqueous tungstate-dye complex adjusted to and buffered at pH 3, increases the sensitivity of the assay to low to trace amounts of protein in the sample. TABLE V demonstrates a further improvement in the assay of urine for low to trace amounts of protein, wherein a concentration of 10 mg/dL of albumin in a test sample readily can be differentiated from a control sample containing 0 mg/dL albumin, and wherein a concentration of 5 mg/dL of albumin in a test sample readily can be differentiated from a control sample containing 0 mg/dL albumin. TABLE V shows that the color space difference between a test sample containing 10 mg/dL protein and a blank test sample (0 mg/dL) is approximately 16 units, and the color space difference between a test sample containing 5 mg/dL protein and a blank test sample is approximately 9 units. Such a color space difference can be detected by the human eye. Therefore, in a test sample containing 5 mg/dL of albumin compared to a blank test sample gives a color space difference of about 5 units, or about one color block. This is a sufficient color space difference to allow the detection and measurement of a trace amount of urine protein because the color space difference is above the threshold of human eye differentiation. In addition, TABLE V shows that a test sample containing 10 mg/dL of albumin can be differentiated from a test sample containing 5 mg/dL of albumin as the color space difference between samples having these albumin levels is approximately 8, or above the threshold of human eye differentiation.

The data included in TABLE V was generated from test strips comprising Whatman CCP500 filter impregnated with an aqueous solution including 30 mg/dL pyrocatechol violet, 75 mg/dL ammonium tungstate and 250 mM (millimolar) glycine buffer to pH 3. TABLE V also shows the color space differences achieved after a two minute reaction time.

TABLE V

COLOR SPACE DIFFERENCES ($\Delta E$) FOR TUNGSTATE-DYE COMPLEX INDICATOR REAGENT COMPOSITIONS USING INCREASED AMOUNT OF TUNGSTATE AND DYE TO VARYING ALBUMIN CONCENTRATIONS

| Reaction Time | $\Delta E$ (Alb 5-0) | $\Delta E$ (Alb 10-0) | $\Delta E$ (Alb 10-5) | $\Delta E$ (Alb 20-0) | $\Delta E$ (Alb 20-10) | $\Delta E$ (Alb 30-0) | $\Delta E$ (Alb 100-0) |
|---|---|---|---|---|---|---|---|
| 2 min. | 9.1 | 15.9 | 8.2 | 23.2 | 7.6 | 25.9 | 32.8 |

It should be understood that those skilled in the art of designing test kits are able to design an optimal test strip incorporating a sufficient amount and a particularly effective tungstate-dye indicator reagent system to permit the detection and measurement of 5 mg/dL of albumin in a test sample, as present tests utilizing the method and composition of the present invention show a color space difference of approximately 5 units. This $\Delta E$ value is almost sufficient for detection by the human eye, and can be detected by present day colorimeters and/or spectrophotometers. Similarly, the method and composition of the present invention will allow differentiation between a test samples containing 10 mg/dL of albumin and a test sample containing 5 mg/dL of albumin, or between test samples having 15 mg/dL and 10 mg/dL of albumin.

In accordance with another important feature of the present invention, it has been found that full color development of test strips containing the tungstate-dye complex as an indicator occurs within about 1 min. to about 2 min. after contacting the test strip with the test sample. Maximum color development, shown in TABLE V, occurs after about 2 min. of contact. However, acceptable and trustworthy assay results are achieved when the test strip is examined for a color change about one minute after contact with the test sample. Only a slight, and visually indetectable, variation in color development occurs between one and two minutes. Such a short time for full color development of the test strip is an additional advantage of the tungstate-dye complex of the present invention over the molybdate-dye complex of the prior art that required approximately 10 minutes for maximum color development. Therefore, test strips incorporating the tungstate-dye indicator reagent composition of the present invention can be used to obtain faster assays and potentially more accurate assays, especially in comparison to assays wherein a molybdate-dye complex based test strip is examined for a color response in less than the 10 min. reaction period. In this case, the maximum color transition has not occurred, thereby providing erroneous assay results. It should be noted that for all of the protein assays summarized in the tables, except for TABLE V, the test strips incorporating the tungstate-dye complex were examined for a color response after a 1.5 minute contact time with the test sample and molybdate-dye complex assays were examined for a response after a 2 minute contact time. It also has been found that the color transition resulting from an albumin and tungstate-dye complex interaction is stable over time.

From TABLE V it is seen that a urine sample containing the trace amount of 5 mg/dL of albumin may be assayed by visual detection and measurement methods, because the color space difference is practically at the minimum required for differentiation by the human eye. Similarly, the $\Delta E$ values of TABLE V, especially $\Delta E$(Alb 10-5), and $\Delta E$(Alb 15-10) show how an increased amount of ammonium tungstate in the tungstate-dye complex provides an indicator reagent composition of heightened sensitivity to the protein content, and especially to the low to trace protein content, of a liquid test sample.

Overall, TABLES II through V show that a tungstate-dye indicator reagent composition impregnated into a suitable carrier matrix, such as filter paper, improves color resolution between test samples having different protein concentrations and improves assay sensitivity for the total protein content of a liquid test sample, especially at low protein levels of less than 30 mg/dL. In addition to the increased sensitivity of the method and composition of the present invention over the prior art molybdate-dye complex method, the composition of the present invention is not subject to ionic strength or specific gravity interferences, and provides full color development and accurate assay results in a much shorter time. The method and composition of the present invention also allows visual differentiation of color transitions resulting from contact of the carrier matrix impregnated with the tungstate-dye complex indicator reagent composition with a test sample containing protein levels of between 0 mg/dL and 10 mg/dL and down to 5 mg/dL, thereby providing accurate and trustworthy assays of test samples containing low to trace amounts of protein.

Therefore, in accordance with an important feature of the present invention, more accurate and reliable assays for total protein content, for low molecular weight protein content and especially for low to trace total protein content in urine and other liquid test samples can be performed by utilizing a tungstate-dye complex indicator reagent composition. The tungstate-dye indicator reagent composition improves the color resolution between protein concentrations and therefore improves assay sensitivity, especially at low to trace albumin levels of approximately 15 mg/dL and below.

Obviously, many modifications and variations of the invention as hereinbefore set forth can be made without departing from the spirit and scope thereof and therefore only such limitations should be imposed as are indicated by the appended claims.

I claim:

1. A composition capable of exhibiting a sufficient color transition upon contacting a protein-containing liquid test sample to show the presence and/or concentration of protein in the test sample at protein concentration levels in the range of 0-2000 mg/dL, said composition consisting essentially of a water-soluble tungstate; a polyhydroxybenzenesulfonephthalein-type dye and/or a polyhydroxybenzenephthalein-type dye; and a nonchelating buffer to maintain the composition at an acidic pH.

2. The composition of claim 1 wherein the polyhydroxybenzenesulfonephthalein-type dye or polyhydroxybenzenephthalein-type dye is selected from the group consisting of pyrocatechol violet, pyrogallol red, bromopyrogallol red, xylenol orange, pyrogallol phthalein and o-hydroxyhydroquinonphthalein; or combinations thereof.

3. The composition of claim 1 wherein the buffer is selected from the group consisting of lactate, phthalate, trichloroacetate, sulfosalicylate, phosphates, acetates, sodium chloride/hydrochloric acid, piperazine-N,N'-bis(2-hydroxypropane)sulfonic acid (POPSO), N-2-hydroxyethyl-piperazine-N'-2-ethanesulfonic acid (HEPES), 3-N-(tris-hydroxymethyl)methylamino-2-hydroxypropanesulfonic acid (TAPSO), and 2-([tris-(hydroxymethyl)methyl]-amino)ethanesulfonic acid (TES); or mixtures thereof.

4. The composition of claim 1 buffered in a pH range of approximately 2 to approximately 4.

5. A composition of claim 1 exhibiting a sufficient color transition within 5 minutes of contacting a protein-containing liquid test sample to show the presence and/or concentration of protein in the test sample.

6. A composition of claim 1 exhibiting a sufficient color transition within 2 minutes of contacting a protein-containing liquid test sample to show the presence and/or concentration of protein in the test sample.

7. The composition of claim 1 wherein the water-soluble tungstate is selected from the group consisting of ammonium tungstate, ammonium paratungstate, bismuth tungstate, cadmium tungstate, calcium tungstate, lithium tungstate, magnesium tungstate, potassium tungstate, sodium metatungstate, sodium tungstate, strontium tungstate, zinc tungstate, phosphotungstates having an alkali metal and/or an ammonium and/or an alkyl, dialkyl, trialkyl or tetraalkylammonium cation, alkylammonium or hydroxyalkylammonium tungstates, dialkylammonium or di(hydroxyalkyl)ammonium tungstates, and trialkylammonium or tri(hydroxyalkyl)ammonium tungstates; or combinations thereof.

8. The composition of claim 7 wherein the water-soluble tungstate is selected from the group consisting of ammonium tungstate, potassium tungstate, sodium tungstate, lithium tungstate, strontium tungstate, alkylammonium or hydroxyalkylammonium tungstates, dialkylammonium or di(hydroxyalkyl)ammonium tungstates, and trialkylammonium or tri(hydroxyalkyl)ammonium tungstates; or combinations thereof.

9. The composition of claim 1 wherein the molar ratio of the polyhydroxybenzenesulfonephthalein-type dye and/or polyhydroxybenzenephthalein-type dye to the water-soluble tungstate is within a range of from about 1 to 1 to about 1 to 10.

10. The composition of claim 9 wherein the molar ratio of the polyhydroxybenzenesulfonephthalein-type dye and/or polyhydroxybenzenephthalein-type dye to the water-soluble tungstate is within a range of from about 1 to 2 to about 1 to 5.

* * * * *